United States Patent
Mikata et al.

(10) Patent No.: US 6,844,429 B2
(45) Date of Patent: Jan. 18, 2005

(54) FULLERENE DERIVATIVE AND COMPOSITION COMPRISING THE SAME

(75) Inventors: Yuji Mikata, Kyoto (JP); Toyoji Kakuchi, Sapporo (JP); Shigenobu Yano, Nara (JP)

(73) Assignees: San-Ei Gen F.F.I., Toyonaka (JP); Shigenobu Yana, Nara (JP)

( * ) Notice: Subject to any disclaimer, the term of this patent is extended or adjusted under 35 U.S.C. 154(b) by 0 days.

(21) Appl. No.: 10/466,870
(22) PCT Filed: Jul. 18, 2002
(86) PCT No.: PCT/JP01/06247

§ 371 (c)(1),
(2), (4) Date: Jul. 18, 2003

(87) PCT Pub. No.: WO02/057285

PCT Pub. Date: Jul. 25, 2002

(65) Prior Publication Data

US 2004/0067892 A1 Apr. 8, 2004

(30) Foreign Application Priority Data

Jan. 19, 2001 (JP) ........................................ 2001-012245

(51) Int. Cl.$^7$ .......................... C07H 15/00; C07H 15/18
(52) U.S. Cl. .......................... 536/1.1; 536/4.1; 536/120; 536/17.2; 423/445 B
(58) Field of Search .......................... 536/1.1, 4.1, 120, 536/17.2; 423/445 B

(56) References Cited

FOREIGN PATENT DOCUMENTS

| JP | 9-235235 A | 9/1997 |
| JP | 11-255794 A | 9/1999 |

*Primary Examiner*—Samuel Barts
*Assistant Examiner*—Michael C. Henry
(74) *Attorney, Agent, or Firm*—Birch, Stewart, Kolasch & Birch, LLP

(57) ABSTRACT

A fullerene derivative represented by the formula (I):

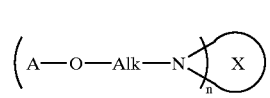

[wherein, A is a residue of monosaccharides or disaccharides, and Alk is a lower alkylene group, the group represented by the formula (X):

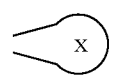

is a fullerene residual skeleton, and n is an integral number of 1 or 2]

or its salt produces a formulation usable for PDT which has more hydrophilicity and lipophilicity, is expected to have selectivity to tumor cells by cell recognition, shows no toxicity to the cells in a dark place and has a cytocidal effect by light irradiation.

4 Claims, 2 Drawing Sheets reaction condition

US 6,844,429 B2

FULLERENE DERIVATIVE AND COMPOSITION COMPRISING THE SAME

This application is the national phase under 35 U.S.C. § 371 of PCT International Application No. PCT/JP01/06247 which has an International filing date of Jul. 18, 2001, which designated the United States of America.

TECHNICAL FIELD

The present invention relates to fullerene derivatives, particularly, fullerene derivatives monosubstituted or disubstituted with monosaccharide or disaccharide residues via an alkylene group or their salts, a method of producing the same and compositions for photosensitization containing the same. Such compositions for photosensitization are usable for the treatment of cancers and tumors.

BACKGROUND ART

The photodynamic therapy(PDT), according to which photosensitizers having a specific affinity for tumor cells are administered to patients before irradiation by laser beams of various wavelengths for treatment of tumors, is now attracting attention as a non-invasive therapy for cancers. PDT enables to exhibit an ability of damaging or killing the tumor cells by excitation of photosensitizers collected to tumor cells at low doses of light irradiation, thus to protect adjacent normal cells from damaging, and to eradicate locally only tumor cells. Known photosensitizers usable for PDT include various derivatives having a porphyrin skeleton or fullerene skeleton, some of which are used clinically.

Desirable photosensitizers usable for PDT are required to be hydrophilic and highly selective to tumor cells and harmless to cells in a dark place. The fullerene derivatives proposed in Japanese Unexamined Patent Publication No. Hei 9-235235 are aimed at directing a target to cancer tissues by enhancing water solubility after modifying fullerene chemically with a water-soluble polymer, polyethylene glycol(PEG). It has been reported that accumulation of a fullerene-PEG combination in cancerous tissues is high when compared with that in normal tissues and that in photodynamic therapy experiments for cancers, masses have disappeared under light irradiation. Since fullerene is chemically modified with PEG, the results concerning enhancement of organic selectivity such as an affinity to cell walls of various organs have not been reported.

Also, Japanese Unexamined Publication No. Hei 11-255794 discloses fullerene derivatives of which fullerene was modified by sugar residues having a protected hydroxyl group. However, the publication does not describe the water solubility of the derivatives and target directivity to cancerous tissues.

DISCLOSURE OF INVENTION

As a result of extensive studies for the development of a better photosensitizer, the present inventors have found that fullerene derivatives having sugar residues for providing hydrophilicity and cell selectivity and having a lower alkylene group for enhancing an affinity to cell walls have a potent photosensitizing action on the light, and to have a strong toxicity against cancer cells, thereby completing the present invention.

BEST MODE FOR CARRYING OUT THE INVENTION

Figure 1:
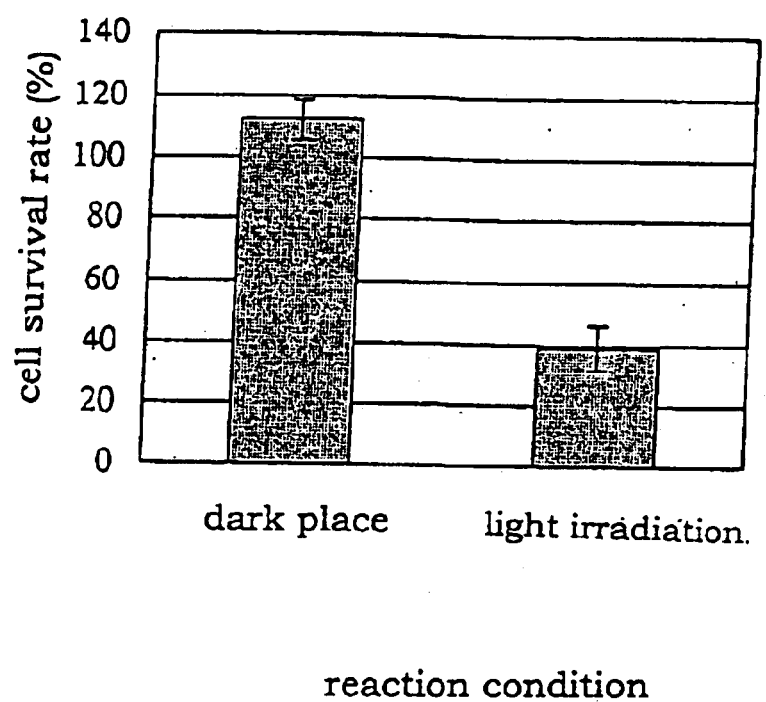
FIG. 1 is a graph showing the toxicity of a fullerene derivative($Mal\text{-}(CH_2)_2\text{-}N)C_{60}$ in the present invention to cells without light irradiation, and with light irradiation.

According to the present invention, provided is a fullerene derivative represented by the formula (I):

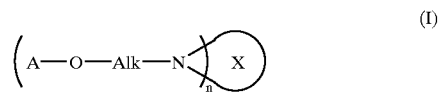

(I)

[wherein, A is a residue of monosaccharides or disaccharides, and Alk is a lower alkylene group, the group represented by the formula (X):

(x)

is a fullerene residual skeleton, and n is an integral number of 1 or 2]
or its salt.

As monosaccharide residues or disaccharide residues may be mentioned the residues derived from monosaccharides such as glucofuranose, glucopyranose, galactopyranose, mannopyranose, and xylopyranose, and disaccharides such as maltose, sucrose and α-lactose.

Preferable examples of monosaccharide residues include: α-D-glucofuranosyl, β-D-glucofuranosyl, α-glucopyranosyl, β-D-glucopyranosyl, α-D-galactopyranosyl, β-D-galactopyranosyl, α-D-mannopyranosyl, β-D-mannopyranosyl, α-D-xylopyranosyl and β-D-xylopyranosyl.

Preferable examples of disaccharide residues include: β-D-glucopyranosyl-(1→4)-D-glucopyranosyl, β-D-fulctofuranosyl-α-D-glucopyranosyl and β-D-galactopyranosyl-(1→4)-α-D-glucopyranosyl.

Lower alkylene groups mean lower alkylene groups having a carbon number of 1 to 6 such as methylene, ethylene, propylene, butylene, pentylene and hexylene, among which ethylene is preferable.

Groups represented by the formula (X) are fullerene residual skeleton, and examples of fullerene as a precursor of fullerene residual skeleton may include fullerene-$C_{60}$, -C$_{70}$, -C$_{76}$, -C$_{78}$, -C$_{82}$, -C$_{84}$, -C$_{90}$, -C$_{96}$ and others. Among them, fullerene-C$_{60}$ is preferable. The fullerene is commercially available. Fullerene residual skeleton may include metals selected from the group 3 elements of the periodic table (e.g., scandium, lanthanum, yttrium), lanthanoids, the group 2 elements and titanium. Fullerene residual skeleton means divalent residues derived from fullerene, and specifically possesses a bonding group at a carbon of a five-numbered ring and a carbon of a six-numbered ring of fullerene.

The fullerene derivatives (I) and their salts of the present invention are preferably a fullerene derivative of the formula (I) in which A is β-D-glucopyranosyl, β-D-mannopyranosyl, β-D-galactopyranosyl, β-D-xylopyranosyl or β-D-glucopyranosyl-(1→4)-D-glucopyranosyl, Alk is an ethylene group, and the group represented by the formula (X) is a residual skeleton of fullerene-C$_{60}$, or its salt.

Specifically, the formula (I-1):

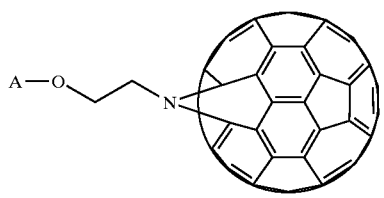

(I-1)

, or the formula (II-1):

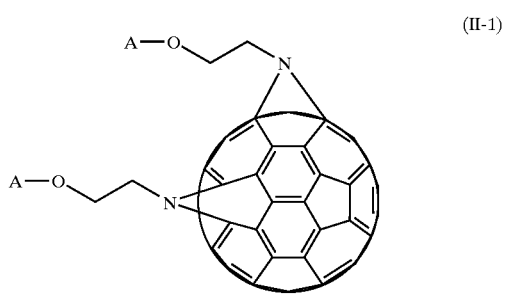

(II-1)

can be given as a representative example.

The fullerene derivatives of the present invention can be prepared according to the method comprising the steps of reacting saccharide all the hydroxyl groups of which are protected with a hydroxyalkylene halide in the presence of Lewis acid, allowing the product to react with sodium azide to obtain an azide compound and allowing it to react with fullerene followed by a deprotection reaction.

In the case in which the saccharide is glucose protected by acetyl groups, and the hydroxyalkyl halide is ethylene bromohydrine, and the fullerene is fullerene-C$_{60}$, the scheme would be as follows:

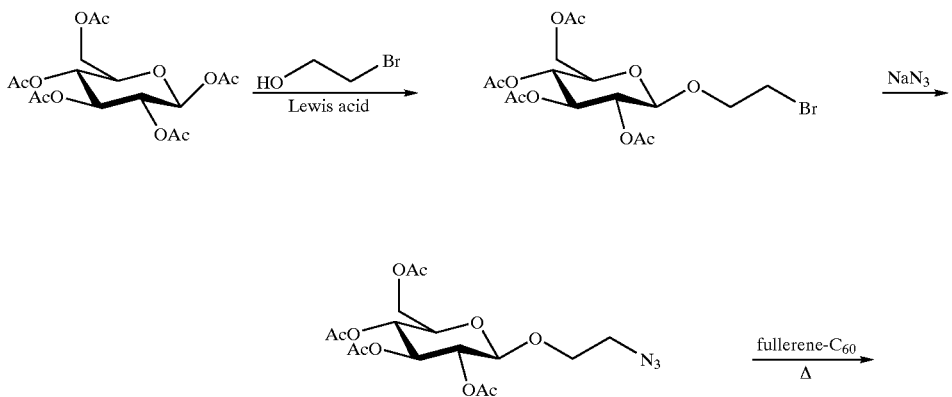

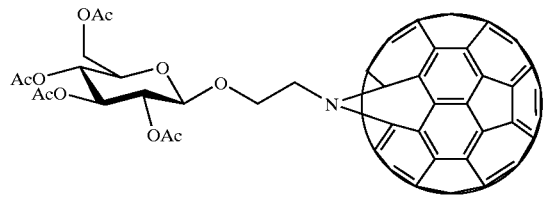

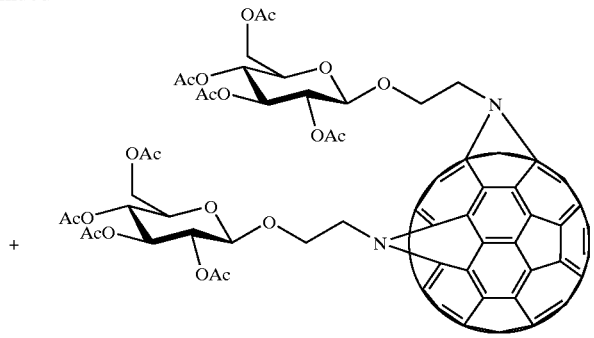

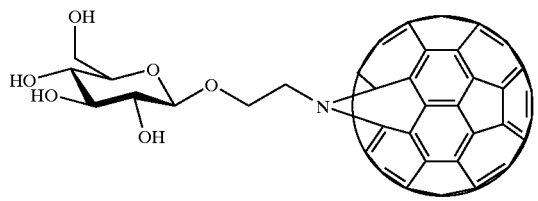

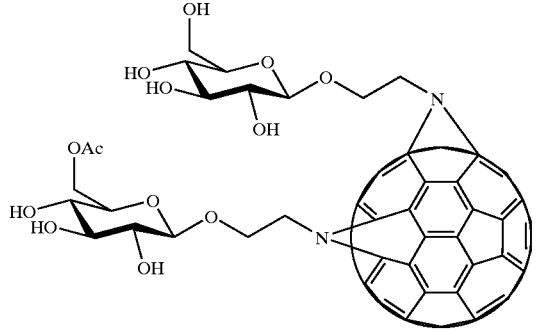

More specifically, one equivalent of glucose in which all the hydroxyl groups of the saccharide are protected is treated in an organic solvent such as dichloromethane at approximately 25° C. in an atmosphere of argon with about one equivalent of ethylene bromohydrine represented by the formula of HO—$(CH_2)_2$—Br in the presence of about 3 equivalents of Lewis acid such as a boron trifluoride diethyl ether complex to obtain a bromide compound. Two equivalents of sodium azide is added to a solution of the bromo compound in a polar organic solvent such as dimethylformamide and the reaction is carried out at 70 to 90° C. for 8 hours in an atmosphere of nitrogen to obtain an azide compound. One equivalent of the obtained azide compound and one equivalent of fullerene are heated under reflux for 8 hours in an atomosphere of nitrogen in a halogenated aromatic hydrocarbon such as chlorobenzene to obtain a mixture of compounds in which one or two sugar residue(s) having protected all the hydroxyl groups of saccharide is added. Each compound in the mixture is fractioned and the protecting groups of the hydroxyl groups of saccharide are released to obtain a compound to which one sugar residue is added and a compound to which two sugar residues are added respectively.

Examples of the protecting groups of the hydroxyl groups include acyl groups such as acetyl and benzoyl, and aralkyl groups such as benzyl. These protecting groups can be released easily according to conventional methods.

The compounds of the present invention can be prepared according to the above-mentioned method with the use of other kinds of saccharide, hydroxyalkylene halide and/or fullerene.

The salts formed with acids or bases can be formed by treating fullerene derivatives (I) obtained above with appropriate acids or bases. As acids or bases usable for forming the salts, may be mentioned, for example, mineral acids such as hydrochloric acid, hydrobromic acid, nitric acid, sulfuric acid and the like, organic acids such as toluenesulfonic acid, benzenesulfonic acid and the like, hydroxides, carbonates and hydrogen carbonates of alkali metals and alkali-earth metals (e.g., sodium, potassium, calcium and magnesium), or ammonium or organic bases such as trimethylamine, triethylamine and the like.

The fullerene derivatives (I) and their salts of the present invention are more hydrophilic and lipophilic due to the introduction of the sugar residues and lower alkylene groups and are expected to have selectivity to tumor cells by cell recognition due to the sugar residues. Furthermore, because they are not toxic to the cells in a dark place, and have a cytocidal effect caused by light irradiation, the fullerene derivatives (I) and their salts of the present invention are useful as photosensitizers for PDT.

Accordingly, the present invention provides compositions for photosensitization comprising the fullerene derivatives (I) and their salts.

The compositions comprising the fullerene derivatives (I) or their salts of the present invention can be used as photosensitizers for treatment of cancers and tumors. Examples of cancers and tumors include stomach cancer, intestinal cancer, lung cancer, breast cancer, uterine cancer, esophageal cancer, ovarian cancer, pancreatic cancer, pharyngeal cancer, sarcoma, liver cancer, bladder cancer, maxillary cancer, bile duct cancer, lingual cancer, brain tumor, skin cancer, malignant struma, prostatic cancer, parotid cancer, Hodgkin's disease, multiple myeloma, kidney cancer, leukemia and malignant lymphocytoma.

The fullerene derivatives (I) or their salts of the present invention may be administered to human and animals in the form of compositions combined with pharmaceutically acceptable ordinary additives. The compositions of the present invention may further contain other pharmaceuticals optionally.

The compositions of the present invention are administered orally, or parenterally, e.g., by intravenous injection or intramuscular injection. They are orally administered in the form of tablets, pills, powders, granules, fine granules, capsules, liquids, suspensions, emulsions and the like, and parenterally administered in the form of injections, drops, suppositories, ointments, plasters, patches, aerosols and the like.

As pharmaceutically acceptable additives may be used those ordinarily used in the pharmaceutical field depending upon dosage form.

For example, tablets can be produced by adding excipients (lactose, starch, crystalline cellulose, etc.), binders (liquid starch, carboxymethyl cellulose, etc.) and the like, according to conventional methods.

For example, injections or drops can be prepared by dissolving the composition in distilled water for injection as a diluent, properly adding a pH regulator, a buffer (sodium citrate, sodium acetate, sodium phosphate, etc.) and the like, and preparing intravenous, intramuscular, subcutaneous, intracutaneous and intraperitoneal injections or drops according to conventional methods. Preferably, the injections and drops are sterilized and are isotonic with blood.

The dosage of the fullerene derivatives (I) or their salts of the present invention is 0.3 to 30 mg/kg, preferably 3 mg/kg, or 0.2 to 20 mg/kg, preferably 2 mg/kg for treatment of tumors.

When the compositions of the present invention are administered, the fullerene derivatives (I) or their salts are distributed selectively in tumor cells after a certain time period.

For treating tumors, the compositions containing the fullerene derivatives (I) or their salts are administered, and then, a beam light with a wavelength of about 260 nm, for example 240 to 280 nm is applied to the site to be treated.

The light source is not particularly limited, but it is desirable to select and use one selectively emitting a strong light beam within a desired wavelength range. As light sources, a semiconductor laser or light-emitting diode such as a near-infrared laser using gallium-aluminum-arsenic, gallium-indium-arsenic-phosphorus, gallium-phosphorus or gallium-arsenic-phosphorus which emits a laser beam, a gas laser such as krypton ion laser, and a dye laser using styryl, oxazin and xanthene may be mentioned.

Specifically, the irradiation intensity of the light beam may be 10 to 500 mW/cm$^2$, preferably 160 to 500 mW/cm$^2$. The number of times of irradiation with the light beam may be one or more times per day, for example, 1 to 100 times/day, preferably 1 to 10 times/day. The combination of times of the administration of the composition of the present invention with the times of irradiation with the light beam may be such that tumor is reduced significantly.

Further, the fullerene derivatives or their salts of the present invention are also usable as a heat-sensitizing paint. When used as a heat-sensitizing paint, they are mixed with a common oil-soluble paint and/or water-soluble paint or synthetic resin to afford a mixed solution to be applied. By applying the heat-sensitizing paint to the airframe surface of high-speed flying objects used under extreme environments such as a rocket, the temperature of the airframe surface can be measured rapidly and precisely. Accordingly, the heat-sensitizing paint is useful in the shape design of high-speed flying objects.

The process of producing fullerene derivatives (I) of the present invention is now described as below by way of examples and production examples, but the present invention is not limited to these examples.

PRODUCTION EXAMPLE 1

A solution of 9.46 g (24.3 mmol) of penta-O-acetyl-β-D-glucopyranose and 3.04 g (24.3 mmol) of ethylene bromohydrin in 100 mL of dichloromethane was put in a 200 mL round bottom flask in an argon atmosphere. Subsequently, 10 mL of boron trifluoride diethyl ether complex was slowly added dropwise to this solution with stirring. The resulting mixture was continuously stirred with ice cooling for another one hour and then stirred at room temperature overnight while protecting it from light. After the stirring, the color of the reaction solution turned orange. An adequate amount of ethyl acetate was added to the reaction solution, and the organic phase was washed with water, a saturated aqueous sodium hydrogen carbonate and a saturated saline successively. After the organic solution was dried over anhydrous sodium sulfate, the organic phase was filtered, and the solvent was evaporated under reduced pressure to give 2-bromoethyl 2,3,4,6-tetra-O-acetyl-β-D-glucopyranoside in the form of an oil (yield 11.0 g; 100%)

PRODUCTION EXAMPLE 2

2-Bromoethyl 2,3,4,6-tetra-O-acetyl-β-D-mannopyranoside was obtained (yield 11.6 g; 100%) in the same manner as in Production Example 1 except that 10.0 g (25.6 mmol) of penta-O-acetyl-β-D-mannopyranose was used instead of 9.46 g (24.3 mmol) of penta-O-acetyl-β-D-glucopyranose.

PRODUCTION EXAMPLE 3

2-Bromoethyl 2,3,4,6-tetra-O-acetyl-β-D-galactopyranoside was obtained (yield 10.6 g; 100%) in the same manner as in Production Example 1 except that 8.9 g (22.8 mmol) of penta-O-acetyl-β-D-galactopyranose was used instead of 9.46 g (24.3 mmol) of penta-O-acetyl-β-D-glucopyranose.

PRODUCTION EXAMPLE 4

2-Bromoethyl 2,3,6,8,9,13-hepta-O-acetyl-β-(α-D-glucopyranosyl (1→4)-D-glucopyranoside) was obtained (yield 21.3 g;100%) in the same manner as in Production Example 1 except that 19.4 g (51.4 mmol) of octaacetyl-maltose was used instead of 9.46 g (24.3 mmol) of penta-O-acetyl-β-D-glucopyranose.

PRODUCTION EXAMPLE 5

2-Bromoethyl 2,3,4-tri-O-acetyl-β-D-xylopyranoside was obtained (yield 2.78 g; 28.7%) in the same manner as in Production Example 1 except that 8.10 g (25.7 mmol) of tri-O-acetyl-β-D-xylopyranose was used instead of 9.46 g (24.3 mmol) of penta-O-acetyl-β-D-glucopyranose.

PRODUCTION EXAMPLE 6

A solution of 11.0 g (24.2 mmol) of 2-bromoethyl 2,3,4,6-tetra-0-acetyl-β-D-glucopyranoside and 3.64 g (55.0 mmol) of sodium azide in 120 mL of dimethylformamide was put in a 200 mL round bottom flask and stirred at 80° C. in an oil bath overnight. An adequate amount of ethyl acetate was added to this reaction solution, and the organic phase was washed with water, a saturated aqueous sodium hydrogen carbonate and a saturated saline successively. After the organic solution was dried over anhydrous sodium sulfate, the organic phase was filtered, and the solvent was evaporated under reduced pressure to give a product in the form of an oil. The product was recrystallized with ethanol to give 2-azidoethyl 2,3,4,6-tetra-O-acetyl-β-D-glucopyranoside in the form of white powdery crystals (yield 1.68 g; 16.6%).

PRODUCTION EXAMPLE 7

2-Azidoethyl 2,3,4,6-tetra-O-acetyl-α-D-mannopyranoside was obtained (yield 10.2 g;97.1%) in the same manner as in Production Example 6 except that 11.6 g (25.4 mmol) of 2-bromoethyl 2,3,4,6-tetra-O-acetyl-α-D-mannopyranoside was used instead of 11.0 g (24.2 mmol) of 2-bromoethyl 2,3,4,6-tetra-O-acetyl-β-D-glucopyranoside.

PRODUCTION EXAMPLE 8

2-Azidoethyl 2,3,4,6-tetra-O-acetyl-β-D-galactopyranoside was obtained (yield 9.48 g; 97.6%) in the same manner as in Production Example 6 except that 10.6 g (23.3 mmol) of 2-bromoethyl 2,3,4,6-tetra-O-acetyl-β-D-galactopyranoside was used instead of 11.0 g (24.2 mmol) of 2-bromoethyl 2,3,4,6-tetra-O-acetyl-β-D-glucopyranoside.

PRODUCTION EXAMPLE 9

2-Azidoethyl 2,3,6,8,9,13-hepta-O-acetyl-β-(α-D-glucopyranosyl(1-4)-D-glucopyranoside) was obtained (2.04 g; yield 43.0%) in the same manner as in Production Example 6 except that 5.01 g (6.73 mmol) of 2-bromoethyl 2,3,6,8,9,13-hepta-O-acetyl-β-(α-D-glucopyranosyl(1-4)-D-glucopyranoside) was used instead of 11.0 g (24.2 mmol) of 2-bromoethyl 2,3,4,6-tetra-O-acetyl-β-D-glucopyranoside.

PRODUCTION EXAMPLE 10

2-Azidoethyl 2,3,4-tri-O-acetyl-β-D-xylopyranoside was obtained (0.72 g; yield 88.9%) in the same manner as in Production Example 6 except that 0.9 g (2.35 mmol) of 2-bromoethyl 2,3,4-tri-O-acetyl-β-D-xylopyranoside was used instead of 11.0 g (24.2 mmol) of 2-bromoethyl 2,3,4,6tetra-O-acetyl-β-D-glucopyranoside.

Example 1

Reaction of 2-azidoethyl 2,3,4,6-tetra-O-acetyl-β-D-glucopyranoside with Fullerene-$C_{60}$ A solution of 42.9 mg ($1.03 \times 10^{-4}$ mol) of 2-azidoethyl 2,3,4,6-tetra-O-acetyl-β-D-glucopyranoside and 73.4 mg ($1.02 \times 10^{-4}$ mol) of fullerene-$C_{60}$ in 25 mL of chlorobenzene was heated at 140° C. in an oil bath in a nitrogen atmosphere overnight while protecting it from light. The solvent from the resulting mixture of N-[2-(2,3,4,6-tetra-O-acetyl-β-D-glucopyranosyloxy)ethyl][5,6]-azafulleroid (a compound of the formula (I-1) in which A is a 2,3,4,6-tetra-O-acetyl-β-D-glucopyranosyl group, hereafter referred to as (D-AcGlc-$(CH_2)_2$—N)$C_{60}$) and N, Nα-bis[2-(2,3,4,6-tetra-O-acetyl-β-D-glucopyranosyloxy)ethyl] [5,6]-diazafulleroid (a compound of the formula (II-1) in which A is a 2,3,4,6-tetra-O-acetyl-β-D-glucopyranosyl group, hereafter referred to as (D-AcGlc-$(CH_2)_2$—N)$_2C_{60}$) was concentrated under reduced pressure. Then, the residue was dissolved in toluene (15 mL) and the resulting solution was purified by silica gel column chromatography eluting with toluene:ethyl acetate= 10:3, 2:1 and 1:1 for separation of 21.7 mg (yield 9%) of (D-AcGlc-$(CH_2)_2$—N)$C_{60}$ and 22.4 mg (yield 29%) of (D-AcGlc-$(CH_2)_2$—N)$_2C_{60}$.

(D-AcGlc-$(CH_2)_2$—N)$C_{60}$ $^1$H NMR (300.07 MHz, CDCl$_3$): δ 2.03 (s, 3H, CH$_3$), 2.05 (s, 3H, CH$_3$), 2.08 (s, 3H, CH$_3$), 2.12 (s, 3H, CH$_3$), 3.77–3.83 (m, 1H, H-5), 4.04 (t, J=6.00 Hz, 2H, H-β1,H-β2), 4.16–4.22 (m, 2H, H-6a, H-α1), 4.31–4.41 (m, 2H, H-6b, H-α2), 4.83 (d, J=7.50 Hz, 1H, H-1), 5.11 (t, J=9.30 Hz, 1H, H-2), 5.17 (t, J=9.60 Hz, 1H, H-4), 5.28 (t, J=9.30, 9.60 Hz, 1H, H-3).

$^{13}$C NMR (75.45 MHz, CDCl$_3$): δ 20.39, 20.52, 20.72, 29.57, 51.24, 61.87, 68.30, 71.14, 71.86, 72.86, 100.85, 125.37, 128.30, 128.63, 129.01, 129.14, 130.52, 130.84, 131.73, 132.62, 134.35, 135.05, 135.16, 135.57, 136.80, 137.56, 137.93, 138.32, 138.80, 139.11, 139.51, 139.59, 139.79, 140.35, 140.71, 140.89, 141.54, 141.68, 141.75, 142.02, 142.41, 142.72, 142.81, 143.48, 143.53, 143.77, 143.85, 144.00, 144.06, 144.02, 144.17, 144.25, 144.38, 144.42, 144.67, 144.71, 144.77, 144.88, 145.06, 145.16, 145.42, 145.60, 146.76, 146.83, 147.59, 147.65, 1620437, 169.52, 170.41, 170.82.

m/z=1110.0(calcd. for $C_{76}H_{23}O_{10}N$ 1110.02).

UV (DMSO) λmax 265, 323, 369 (nm).

IR (KBr) 1756, 1428, 1363, 1220, 1044, 527cm$^{-1}$.

(D-AcGlc-$(CH_2)_2$—N)$_2C_{60}$ $^1$H NMR (300.07 MHz, CDCl$_3$): δ 2.04(s), 2.05(s), 2.07(s), 2.10(s), 2.11(s), 2.12 (s), 3.78–3.85(dd, 2H), 4.05–4.26(m), 4.33–4.45(m), 4.74–4.81(d,2H), 5.10–5.31(m).

$^{13}$C NMR (75.45 MHz, CDCl$_3$): δ 20.49, 20.67, 20.73, 20.81, 20.93, 21.33, 50.97, 51.26, 60.34, 61.81, 61.89, 68.22, 68.31, 68.56, 71.22, 71.31, 71.94, 72.89, 72.97, 100.67, 100.73, 125.36, 128.29, 129.11, 130.53, 130.86, 131.75, 132.64, 134.37, 135.08, 135.18, 135.60, 136.81, 137.59, 137.96, 138.32, 138.82, 139.14, 139.59, 139.63, 139.82, 140.40, 140.73, 140.89, 141.57, 141.71, 141.78, 142.05, 142.44, 142.73, 142.85, 143.16, 143.51, 143.80, 143.88, 144.01, 144.09, 144.14, 144.20, 144.29, 144.45, 144.71, 144.76, 144.92, 145.09, 145.19, 145.45, 145.63, 146.77, 146.84, 147.60, 147.67, 162.45, 169.60, 170.43, 170.46, 170.87, 171.34.

m/z=1499.3(calcd. for $C_{92}H_{46}O_{20}N_2$ 1499.38).

UV (DMSO) λmax 265, 325, 370 (nm).

IR (KBr) 1755, 1430, 1365, 1229, 1037, 527cm$^{-1}$.

Example 2

Reaction of 2-azidoethyl 2,3,4,6-tetra-O-acetyl-α-D-mannopyranoside with $C_{60}$.

17.6 mg (yield 19%) of N-[2-(2,3,4,6-tetra-O-acetyl-α-D-mannopyranosyloxy)ethyl] [5,6]-azafulleroid (a compound of the formula (I-1) in which A is a 2,3,4,6-tetra-O-acetyl-α-D-mannopyranosyl group, hereafter referred to as (D-AcMan-$(CH_2)_2$—N)$C_{60}$) and 18.1 mg (yield 29%) of N, N'-bis [2-(2,3,4,6-tetra-O-acetyl-α-D-mannopyranosyloxy) ethyl] [5,6]-diazafulleroid (a compound of the formula (II-1) in which A is a 2,3,4,6-tetra-O-acetyl-α-D-mannopyranosyl group, hereafter referred to as (D-AcMan-$(CH_2)_2$—N)$_2C_{60}$) were obtained in the same manner as in Example 1 except that 35 mg ($8.39 \times 10^{-5}$ mol) of 2-azidoethyl 2,3,4,6-tetra-O-acetyl-α-D-mannopyranoside and 60 mg ($8.33 \times 10^{-5}$ mol) of fullerene-C60 were used instead of 42.9 mg ($1.03 \times 10^{-4}$ mol) of 2-azidoethyl 2,3,4,6-tetra-O-acetyl-α-D-glucopyranoside and 73.4 mg ($1.02 \times 10^{-4}$ mol) of fullerene-$C_{60}$.

(D-AcMan-$(CH_2)_2$—N)$C_{60}$ $^1$H NMR (300.07 MHz, CDCl$_3$): δ 2.00 (s, 3H, CH$_3$), 2.03 (s, 3H, CH$_3$), 2.13 (s, 3H, CH$_3$), 2.19 (s, 3H, CH$_3$), 4.01–4.09(m, 2H, H-β1, H-β2), 4.17–4.25 (m, 2H, H-6a, H-α1), 4.31–4.36 (m, 3H, H-5, H-6b, H-α2), 5.06 (s, 1H, H-1), 5.34–5.38 (m, 3H, H-2, H-3, H-4).

$^{13}$C NMR (75.45 MHz, CDCl$_3$): δ 20.59, 20.68, 20.73, 20.81, 29.60, 51.50, 62.50, 66.13, 67.33, 68.98, 69.46, 97.66, 125.37, 128.30, 128.71, 129.13, 130.97, 134.03, 136.08, 136.23, 136.70, 137.94, 138.06, 138.51, 138.69, 139.53, 140.55, 140.99, 141.63, 142.88, 143.06, 143.20, 143.27, 143.38, 143.56, 143.75, 144.01, 144.29, 144.43, 144.54, 144.71, 144.82, 145.03, 145.98, 147.86, 147.97, 169.90, 170.27, 170.83.

m/z=1109.6(calcd. for $C_{76}H_{23}O_{10}N$ 1110.02).

UV (DMSO) λmax 265, 334, 370 (nm).

IR (KBr) 1749, 1431, 1365, 1262, 1037, 527cm$^{-1}$.

(D-AcMan-$(CH_2)_2$—N)$_2C_{60}$ $^1$H NMR (300.07 MHz, CDCl$_3$): δ,1.99, 2.00, 2.01, 2.02, 2.04 (s), 2.06, 2.09, 2.10, 4.09–4.32(m), 5.07–5.11(dd), 5.27–5.58(m).

$^{13}$C NMR (75.45 MHz, CDCl$_3$): 20.51, 20.55, 20.72, 20.75, 49.45, 50.63, 62.00, 62.33, 65.43, 65.77, 66.03, 67.12, 68.25, 68.25, 69.17, 69.35, 70.53, 90.56, 97.26, 97.66, 125.32, 128.27, 129.08, 130.28, 131.12, 132.43, 132.83, 132.93, 133.85, 135.08, 135.60, 135.95, 136.16, 136.92, 137.93, 137.99, 138.72, 139.32, 139.43, 139.48, 139.51, 139.79, 139.92, 141.07, 141.52, 141.76, 141.83, 141.86, 141.89, 142.67, 142.75, 142.89, 143.38, 143.51, 143.56, 143.88, 143.91, 143.96, 143.99, 144.12, 144.19, 144.56, 144.63, 144.69, 144.74, 144.79, 144.87, 144.97, 145.09, 145.18, 145.22, 145.58, 145.71, 146.73, 147.04, 147.52, 147.63, 162.07, 168.20, 169.67, 169.78, 169.88, 170.12, 170.37, 170.74, 170.79.

m/z=1499.5(calcd. for $C_{92}H_{46}O_{20}N_2$ 1499.38).

UV (DMSO) λmax 266, 328, 370 (nm).

IR (KBr) 1753, 1431, 1370, 1221, 1047, 526cm$^{-1}$.

Example 3

Reaction of 2-azidoethyl 2,3,4,6-tefra-O-acetyl-β-D-galactopyranoside with Fullerene-$C_{60}$ 30.1 mg (yield 14%) of N-[2-(2,3,4,6-tetra-O-acetyl-β-D-galactopyranosyloxy)ethyl] [5,6]-azafulleroid (a compound of the formula (I-1) in which A is a 2,3,4,6-tetra-O-acetyl-β-D-galactopyranosyl group, hereafter referred to as (D-AcGal-$(CH_2)_2$—N)$C_{60}$) and 27.6 mg (yield 19%) of N, N'-bis[2-(2,3,4,6-tetra-O-acetyl-β-D-galactopyranosyloxy)ethyl] [5,6]-diazafulleroid (a compound of the formula (II-1) in which A is a 2,3,4,6-tetra-O-acetyl-β-D-galactopyranosyl group, hereafter referred to as (D-AcGal-$(CH_2)_2$—N)$_2C_{60}$) were obtained in the same manner as in Example 1 except that 81 mg (1.94×10$^{-4}$ mol) of 2-azidoethyl 2,3,4,6-tetra-O-acetyl-β-D-galactopyranoside and 141 mg (1.96×10$^{-4}$ mol) of fullerene-$C_{60}$ were used instead of 42.9 mg (1.03×10$^{-4}$ mol) of 2-azidoethyl 2,3,4,6-tetra-O-acetyl-β-D-glucopyranoside and 73.4 mg (1.02×10$^{-4}$ mol) of fullerene-$C_{60}$.

(D-AcGal-$(CH_2)_2$—N)$C_{60}$ $^1$H NMR (300.07 MHz, CDCl$_3$): δ 2.00 (s, 3H, CH$_3$), 2.08 (s, 3H, CH$_3$), 2.09 (s, 3H, CH$_3$), 2.19 (s, 3H, CH$_3$), 3.99–4.07(m, 3H, H-5, H-μ1, H-β2), 4.15–4.28 (m, 3H, H-6a, H-α1, H-α2), 4.37 (dd, J=5.01 10.50, 1H, H-6b), 4.79 (d, J=8.10, 1H, H=1), 5.09 (dd, J=3.30, 10.80 Hz, 1H, H-3), 5.33 (dd, J=8.10, 10.50 Hz, 1H, H-2), 5.44 (d, J=2.70 Hz, 1H, H-4).

$^{13}$C NMR (75.45 MHz, CDCl$_3$): δ 20.49, 20.60, 20.93, 20.86, 29.60, 51.28, 61.16, 66.99, 68.18, 68.81, 70.76, 101.25, 121.96, 125.96, 128.56, 129.77, 130.92, 131.85, 132.09, 132.62, 133.77, 135.21, 135.61, 135.80, 136.93, 137.82, 138.46, 138.87, 139.30, 139.66, 140.79, 140.95, 141.83, 142.13, 142.09, 143.54, 143.75, 143.92, 144.09, 144.12, 144.32, 144.48, 144.67, 144.77, 144.83, 145.31, 145.45, 145.71, 146.91, 147.42, 147.63, 162.44, 169.60, 170.35, 170.46, 170.58.

m/z=1109.1(calcd. for $C_{76}H_{23}O_{10}N$ 1110.02).

UV (DMSO) λmax 266, 328,370 (nm).

IR (KBr). 1750, 1430, 1367, 1262, 1047, 525cm$^{-1}$.

(AcGal-$(CH_2)_2$—N)$_2C_{60}$ $^1$H NMR (300.07 MHz, CDCl$_3$): δ 2.00, 2.01, 2.07, 2.07, 2.08, 2.12(s), 2.19(s),2.21(s), 3.99–4.47(m), 4.73(d, J=8.10 Hz, 1H, H-1a), 4.80(d, J=8.10 Hz, 1H, H-1b), 5.076–5.122 (dd, 2H), 5.30–5.365(m, 2H), 5.44–5.45(m, 2H).

$^{13}$C NMR (75.45MHz, CDCl$_3$): δ 20.47, 20.59, 20.85, 20.91, 51.23, 60.97, 61.11, 66.92, 66.99, 68.17, 68.30, 68.75, 68.86, 70.71, 70.95, 101.15, 101.20, 130.55, 130.89, 131.81, 132.59, 134.40, 135.05, 135.16, 135.60, 136.86, 137.56, 138.41, 138.82, 139.14, 139.56, 139.63, 139.80, 140.32, 140.60, 140.94, 141.55, 141.68, 141.78, 142.05, 142.41, 142.72, 142.80, 143.51, 143.54, 143.75, 143.90, 144.03, 144.09, 144.14, 144.19, 144.27, 144.42, 144.74, 144.79, 144.92, 145.09, 145.18, 145.42, 145.61, 146.78, 146.86, 147.60, 147.67, 162.42, 169.57, 169.60, 170.32, 170.45, 170.51, 170.54.

m/z=1109.1(calcd. for $C_{76}H_{23}O_{10}N$ 1110.02).

UV (DMSO) λmax 266, 329, 370 (nm).

IR (KBr) 1752, 1430, 1371, 1226, 1077, 527cm$^{-1}$.

Example 4

Reaction of 2-azidoethyl 2,3,6,8,9,13-hepta-O-acetyl-β-(α-D-glucopyranosyl(1-4)-D-glucopyranoside) with Fullerene-$C_{60}$ 24.5 mg (yield 17%) of N-[2-(2,3,6,8,9,13-hepta-O-acetyl-β-(α-D-glucopyranosyl (1-4)-D-glucopyranosyloxy) ethyl] [5,6]-azafulleroid (a compound of the formula (I-1) in which A is a 2,3,6,8,9,13-hepta-O-acetyl-β-(α-D-glucopyranosyl (1-4)-D-glucopyranosyl) group, hereafter referred to as (D-AcMal-(CH2)2—N)$C_{60}$) and 36.4 mg (yield 34%) of N, N'-bis[2-(2,3,6,8,9,13-hepta-O-acetyl-β-(α-D-glucopyranosyl (1-4)-D-glucopyranosyloxy)ethyl) [5,6]-diazafulleroid (a compound of the formula (II-1) in which A is a 2,3,6,8,9,13-hepta-O-acetyl-β-(α-D-glucopyranosyl(1-4)-D-glucopyranosyl group, hereafter referred to as (D-AcMal-(CH2)2—N)2C60)) were obtained in the same manner as in Example 1 except that 72.7 mg (1.03×10–4mol) of 2-azidoethyl 2,3,6,8,9,13-hepta-O-acetyl-β-(α-D-glucopyranosyl(1-4)-D-glucopyranoside) and 75.1 mg (1.04×10$^{-4}$mol) of fullerene-$C_{60}$ were used instead of 42.9 mg (1.03×10$^{-4}$mol) of 2-azidoethyl 2,3,4,6-tetra-O-acetyl-β-D-glucopyranoside and 73.4 mg (1.02×10$^{-4}$mol) of fullerene-$C_{60}$.

(AcMal-$(CH_2)_2$—N)$C_{60}$ $^1$H NMR (300.07 MHz, CDCl$_3$): δ 2.01 (s, 3H, CH$_3$) 2.02 (s, 3H, CH$_3$), 2.03 (s, 3H, CH$_3$), 2.05 (s, 3H, CH$_3$),2.06(s, 3H, CH$_3$), 2.11(s, 3H, CH$_3$), 2.18(s, 3H, CH$_3$), 3.77–3.81(m, H1, H-5), 3.96–4.17 (m, 6H, H-4, H-11, H-12a, H-α1, H-β1, H-,2), 4.24–4.38 (m, 3H, H=6a, H-12b, H-α2), 4.55 (dd, 1H, H-6b),4.82–4.98 (m, 3H, H-1, H-2, H-8), 5.07(t, 9.90 Hz, 1H, H-10).

$^{13}$C NMR (75.45 MHz, CDCl$_3$): δ 20.47, 20.60, 20.83, 29.60, 51.63, 61.44, 62.80, 67.96, 68.47, 68.70, 69.32, 69.98, 72.28, 72.65, 75.45, 95.61, 100.54, 133.85, 134.34, 134.60, 134.97, 135.44, 135.87, 135.95, 136.00, 136.08, 136.34, 136.79, 136.94, 137.09, 137.17, 137.62, 137.75, 137.99, 138.27, 138.48; 138.66, 138.95, 139.43, 139.50, 139.92, 140.14, 140.92, 141.57, 142.47, 142.85, 143.06, 143.25, 143.36, 143.56, 143.79, 143.99, 144.15, 144.19, 144.30, 144.46, 144.59, 144.76, 144.87, 145.13, 145.32, 145.35, 145.92, 146.11, 146.21, 146.31, 146.92, 147.88, 169.60, 169.90, 170.17, 170.46, 170.74.

m/z=1397.7(calcd. for $C_{88}H_{39}O_{18}N$ 1398.27).

UV (DMSO) λmax266, 326, 370(nm).

IR (KBr) 1750, 1436, 1367, 1232, 1044, 527 cm$^{-1}$.

(AcMal-$(CH_2)_2$—N)$_2C_{60}$ $^1$H NMR (300.07 MHz, CDCl$_3$): δ2.01, 2.02, 2.03, 2.05, 2.07, 2.09, 2.11, 3.76–3.79(m), 3.88–4.60(m), 4.74–5.58(m).

$^{13}$C NMR (75.45 MHz, CDCl$_3$): δ, 20.43, 20.55, 20.76, 50.95, 51.08, 61.36, 62.75, 67.91, 68.22, 68.41, 68.67, 69.27, 69.93, 72.08, 72.13, 72.26, 72.44, 72.57, 72.73, 75.27, 75.46, 95.59, 100.15, 100.28, 130.50, 130.76, 131.83, 132.54, 134.37, 135.02, 135.16, 135.53, 136.80, 137.49, 138.38, 138.82, 139.14, 139.53, 139.59, 139.77, 140.27, 140.53, 140.79, 141.52, 141.66, 141.75, 142.02, 142.38, 142.70, 142.78, 143.48, 143.53, 143.75, 143.88, 143.99, 144.08, 144.12, 144.17, 144.25, 144.37, 144.67, 144.72, 144.77, 144.90, 145.05, 145.09, 145.18, 145.40, 145.60, 146.78, 146.83, 147.59, 147.63, 162.34, 169.56, 169.83, 170.12, 170.38, 170.59, 170.67.

m/z=2076.7(calcd. for C$_{116}$H$_{78}$O$_{36}$N$_2$ 2075.89).

UV (DMSO) λmax 265, 327, 370 (nm).

IR (KBr) 1756, 1431, 1369, 1234, 1047, 520cm$^{-1}$.

Example 5

Reaction of 2-azidoethyl 2,3,4-tri-O-acetyl-β-D-xylopyranoside with Fullerene-C$_{60}$ 5.23 mg (yield 14%) of N-[2-(2,3,4-tri-O-acetyl-β-D-xylopyranosyloxy)ethyl] [5,6]-azafulleroid (a compound of the formula (I-1) in which A is a 2,3,4-tri-O-acetyl-β-D-xylopyranosyl group, hereafter referred to as (D-AcXyl-(CH$_2$)$_2$—N)C$_{60}$) and 12.2 mg (yield 50%) of N,Nα-bis[2-(2,3,4-tri-O-acetyl-β-D-xylopyranosyloxy)ethyl] [5,6]-diazafulleroid (a compound of the formula (II-1) in which A is a 2,3,4-tri-O-acetyl-β-D-xylopyranosyl group, hereafter referred to as (D-AcXyl-(CH$_2$)$_2$—N)$_2$C$_{60}$) were obtained in the same manner as in Example 1 except that 12.4 mg (3.60×10$^{-5}$ mol) of 2-azidoethyl 2,3,4-tri-O-acetyl-β-D-xylopyranoside and 26.6 mg (3.69×10$^{-5}$ mol) of fullerene-C$_{60}$ were used instead of 42.9 mg (1.03×10$^{-4}$ mol) of 2-azidoethyl 2,3,4,6-tetra-O-acetyl-β-D-glucopyranoside and 73.4 mg (1.02×10$^{-4}$ mol) of fullerene-C$_{60}$.

(D-AcXyl-(CH$_2$)$_2$—N)C$_{60}$ $^1$H NMR (300.07 MHz, CDCl$_3$): δ2.06 (s, 3H, CH$_3$), 2.07 (s, 3H, CH$_3$), 2.09 (s, 3H, CH$_3$), 3.48 (dd, J=8.40, 12.00 Hz, 1H, H-5a), 4.02–4.37(m, 5H, H-5b, H-α1, H-α2, H-β1, H-β2), 4.79 (d, J=6.90 Hz, 1H, H-1), 4.97–5.08 (m, 2H, H-2, H-4), 5.23 (t, J=8.10, 8.40 Hz, 1H, H-3).

$^{13}$C NMR (75.45 MHz, CDCl$_3$): δ 20.65, 20.78, 29.58, 51.73, 62.12, 68.88, 70.71, 71.37, 100.91, 128.72, 128.88, 129.79, 130.11, 130.97, 131.20, 133.85, 134.98, 135.88, 135.99, 136.37, 136.84, 136.99, 137.64, 137.95, 138.00, 138.28, 138.64, 139.42, 140.66, 140.79, 140.90, 141.58, 142.54, 142.83, 143.04, 143.20, 143.25, 143.54, 143.77, 143.98, 144.18, 144.29, 144.45, 144.61, 144.74, 144.85, 145.13, 145.29, 146.19, 146.29, 146.76, 147.93, 169.64, 170.06, 170.28.

m/z=1038.8(calcd. for C$_{73}$H$_{19}$O$_8$N 1038.00).

UV (DMSO) λmax 266, 326, 370 (nm).

IR (KBr) 1756, 1430, 1369, 1221, 1037, 524cm$^{-1}$.

(D-AcXyl-(CH$_2$)$_2$—N)$_2$C$_{60}$ $^1$H NMR (300.07 MHz, CDCl$_3$): δ 2.05(s), 2.05(s), 2.06(s), 2.07(s), 2.09(s), 2.11(s), 3.43–3.52(m), 4.05–4.51(m), 4.71–4.77(dd, 2H), 5.02–5.11(m, 4H), 5.21–5.28(m, 2H).

$^{13}$C NMR (75.45 MHz, CDCl$_3$): δ20.62, 20.73, 20.78, 21.31, 51.02, 51.16, 62.13, 62.29, 67.84, 68.05, 68.31, 68.67, 68.94, 70.84, 70.89, 71.58, 71.76, 100.70, 100.91, 125.34, 128.27, 129.09, 130.57, 130.84, 131.60, 132.61, 132.69, 134.51, 134.89, 135.26, 135.47, 137.04, 137.36, 137.93, 138.79, 138.88, 139.04, 139.55, 139.59, 139.74, 139.79, 140.86, 140.90, 141.66, 141.73, 142.12, 142.33, 142.73, 142.80, 143.15, 143.44, 143.57, 143.72, 143.85, 144.01, 144.04, 144.06, 144.20, 144.29, 144.33, 144.37, 144.71, 144.93, 145.03, 145.09, 145.21, 145.34, 145.58, 146.81, 146.84, 147.65, 162.55, 169.57, 169.62, 170.03, 170.27.

m/z=1356.6(calcd. for C$_{86}$H$_{38}$O$_{16}$N$_2$ 1355.25).

UV (DMSO) λmax 265, 328, 370 (nm).

IR (KBr) 1756, 1369, 1221, 1037, 524cm$^{-1}$.

Example 6

Sodium methoxide was added to 9.5 mg (8.56×10$^{-6}$mol) of (D-AcGlc-(CH$_2$)$_2$—N)C$_{60}$ in 4 mL of a mixture solution of chloroform and methanol (chloroform;methanol=1:1) to adjust the mixture solution to pH 9. The mixture was heated at 70° C. in an oil bath in a nitrogen atmosphere for half an hour while protecting it from light, neutralized with a 25° C. aqueous acetic acid, and then allowed to stand in a refrigerator for three hours. The formed precipitate was collected through filtration using a membrane filter, followed by drying under reduced pressure, to give 6.77 mg (yield 84%) of N-[2-(β-D-glucopyranosyloxy)ethyl] [5,6]-azafulleroid (a compound of the formula (I-1) in which A is an β-D-glucopyranosyl group, hereafter referred to as (D-Glc-(CH2)2—N)C60).

M/z=940.1 (calcd. for C68H14O6N 940.86).

UV (DMSO) λmax 265, 323, 339, 369 (nm)

IR (KBr) 3439, 2924, 1647, 1436, 1082, 528 cm$^{-1}$.

Example 7

14.7mg (yield 69%) of N, N'-bis[2-(β-D-glucopyranosyloxy)ethyl][5,6]-diazafulleroid (a compound of the formula (II-1) in which A is an β-D-glucopyranosyl group, hereafter referred to as (D-Glc-(CH$_2$)$_2$—N)$_2$C$_{60}$) was obtained in the same manner as in Example 6 except that 27.5 mg (1.83×10$^{-5}$ mol) of (D-AcGlc-(CH$_2$)$_2$—N)$_2$C$_{60}$ was used instead of 9.5 mg, (8.56×10$^{-6}$ mol) of (D-AcGlc-(CH$_2$)$_2$—N)C$_{60}$.

m/z=1161.2 (calcd. for C$_{76}$H$_{29}$O$_{12}$N$_2$ 1162.07).

UV (DMSO) λ$_{max}$ 265, 324, 339, 370 (nm).

IR (KBr) 3423, 2918, 1653, 1418, 1078, 531 cm$^{-1}$.

Example 8

10.8 mg (yield 71%) of N-[2-(α-D-mannopyranosyloxy)ethyl] [5,6]-azafulleroid (a compound of the formula (I-1) in which A is an α-D-mannopyranosyl group, hereafter referred to as (D-Man-(CH$_2$)$_2$—N)C$_{60}$) was obtained in the same manner as in Example 6 except that 18.0 mg (1.62×10-5mol) of (D-AcMan-(CH$_2$)$_2$—N)C$_{60}$ was used instead of 9.5 mg (8.56×10$^{-6}$mol) of (D-AcGlc-(CH$_2$)$_2$—N)C$_{60}$.

M/z=940.1 (calcd. for C68H14O6N 940.86).

UV (DMSO) λmax 265, 325, 340, 370 (nm).

IR (KBr) 3447, 2918, 1653, 1418, 1076, 526 cm$^{-1}$.

Example 9

14.8 mg (yield 38%) of N,N'-bis[2-(α-D-mannopyranosyloxy)ethyl] [5,6]-diazafulleroid (a compound of the formula (II-1) in which A is an α-D-mannopyranosyl group, hereafter referred to as (D-Man-(CH$_2$)$_2$—N)2C$_{60}$) was obtained in the same manner as in Example 6 except that 50 mg (3.34×10$^{-5}$mol) of (D-AcMan-(CH$_2$)$_2$—N)2C$_{60}$ was used instead of 9.5 mg (8.56×10$^{-6}$mol) of (D-AcGlc-(CH$_2$)$_2$—N)C$_{60}$.

M/z=1161.2 (calcd. for C$_{76}$H$_{29}$O$_{12}$N$_2$1162.07).

UV (DMSO) λmax 266, 322, 338, 370 (nm)

IR (KBr) 3388, 2918, 1653, 1419, 1056, 530 cm–$^1$.

Example 10

10.0 mg (yield 72%) of N-[2-(β-D-galactopyranosyloxy)ethyl][5,6]-azafulleroid (a compound of the formula (I-1) in which A is an β-D-galactopyranosyl group, hereafter referred to as (D-Gal-(CH$_2$)$_2$—N)C$_{60}$) was obtained in the same manner as in Example 6 except that 16.3 mg (1.47× 10$^{-5}$ mol) of (D-AcGal-(CH$_2$)$_2$—N)C$_{60}$ was used instead of 9.5 mg (8.56×10$^{-6}$ mol) of (D-AcGlc-(CH$_2$)$_2$—N)C$_{60}$.

m/z=940.1 (calcd. for C$_{68}$H$_{14}$O$_6$N 940.86).

UV (DMSO) $\lambda_{max}$ 265, 326, 340, 370 (nm).

IR (KBr) 3418, 2928, 1638, 1415, 1077, 526 cm$^{-1}$.

Example 11

9.60 mg (yield 65%) of N,N'-bis[2-(β-D-galactopyranosyloxy)ethyl] [5,6]-diazafulleroid (a compound of the formula (II-1) in which A is an β-D-galactopyranosyl group, hereafter referred to as (D-Gal-(CH$_2$)$_2$—N)$_2$C$_{60}$) was obtained in the same manner as in Example 6 except that 18.9 mg (1.26×10$^{-5}$mol) of (D-AcGal-(CH2)2—N)2C$_{60}$ was used instead of 9.5 mg (8.56×10$^{-6}$mol) of (D-AcGlc-(CH$_2$)$_2$—N)C$_{60}$.

M/z=1161.2 (calcd. for C$_{76}$H$_{29}$O$_{12}$N$_2$ 1162.07).

UV (DMSO) λmax 265, 324, 340, 370 (nm).

IR (KBr) 3377, 2928, 1638, 1416, 1074, 530 cm$^{-1}$.

Example 12

17.7 mg (yield 86%) of N-[2-(β-(α-D-glucopyranosyl(1-4)-D-glucopyranosyloxy)ethyl] [5,6]-azafulleroid (a compound of the formula (I-1) in which A is an β-(α-D-glucopyranosyl (1-4)-D-glucopyranosyl) group, hereafter referred to as (Mal-(CH$_2$)$_2$—N)C$_{60}$) was obtained in the same manner as in Example 6 except that 26.0 mg (1.86× 10$^{-5}$mol) of (Mal-(CH$_2$)$_2$—N)C$_{60}$ was used instead of 9.5 mg (8.56×10$^{-6}$mol) of (D-AcGlc-(CH$_2$)$_2$—N)C$_{60}$.

☐/z=1126.00 (calcd. for C74H25O11NNa 1127.00).

UV (DMSO) λmax 265, 326, 339, 370 (nm).

IR (KBr) 3419, 2925, 1641, 1428, 1054, 528 cm-1.

Example 13

9.45 mg (yield 66%) of N,N'-bis[2-(β-(α-D-glucopyranosyl(1-4)-D-glucopyranosyloxy)ethyl] [5,6]-diazafulleroid (a compound of the formula (II-1) in which A is an β-(α-D-glucopyranosyl (1-4)-D-glucopyranosyl) group, hereafter referred to as (Mal-(CH$_2$)$_2$—N)$_2$C$_{60}$) was obtained in the same manner as in Example 6 except that 20.0 mg (9.63×10$^{-6}$mol) of (Mal-(CH$_2$)$_2$—N)$_2$C$_{60}$ was used instead of 9.5 mg (8.56×10$^{-6}$mol) of (D-AcGlc-(CH$_2$)2—N)C60.

M/z=1486.3 (calcd. for C$_{88}$H$_{49}$O$_{22}$N$_2$ 1486.36).

UV (DMSO) λmax 265, 323, 337, 370 (nm).

IR (KBr) 3412, 2927, 1643, 1457, 1033, 527 cm$^-$1.

Example 14

2.84 mg (yield 26%) of N-[2-(β-D-xylopyranosyloxy) ethyl][5,6]-azafulleroid (a compound of the formula (I-1) in which A is an β-xylopyranosyl group, hereafter referred to as (D-Xyl-(CH$_2$)$_2$—N)C$_{60}$) was obtained in the same manner as in Example 6 except that 12.5 mg (1.20×10$^{-5}$ mol) of (D-AcXyl-(CH$_2$)$_2$—N)C$_{60}$ was used instead of 9.5 mg (8.56×10$^{-6}$ mol) of (D-AcGlc-(CH$_2$)$_2$—N)C$_{60}$.

m/z=910.1 (calcd. for C$_{67}$H$_{12}$O$_5$N 910.84).

UV (DMSO) $\lambda_{max}$ 265, 324, 339, 370 (nm).

IR (KBr) 3450, 2924, 1644, 1429, 1076, 527 cm$^{-1}$.

Example 15

18.2 mg (yield 71%) of N,N'-bis[2-(β-D-xylopyranosyloxy)ethyl] [5,6]-diazafulleroid (a compound of the formula (II-1) in which A is an β-xylopyranosyl group, hereafter referred to as (D-Xyl-(CH$_2$)$_2$—N)$_2$C$_{60}$) was obtained in the same manner as in Example 6 except that 31.6 mg (2.33×10$^{-5}$ mol) of (D-AcXyl-(CH$_2$)$_2$—N)$_2$C$_{60}$ was used instead of 9.5 mg (8.56×10$^{-6}$ mol) of (D-AcGlc-(CH$_2$)$_2$—N)C$_{60}$.

m/z=1101.2 (calcd. for C$_{74}$H$_{25}$O$_{10}$N$_2$ 1102.02).

UV (DMSO) $\lambda_{max}$ 265, 325, 339, 370 (nm).

IR (KBr) 3374, 2886, 1647, 1419, 1045, 529 cm$^{-1}$.

The compounds prepared in Examples 1 to 15 are represented by the formulae provided in Table 1.

TABLE 1

| Ex. No. | formula |
|---|---|
| 1 | 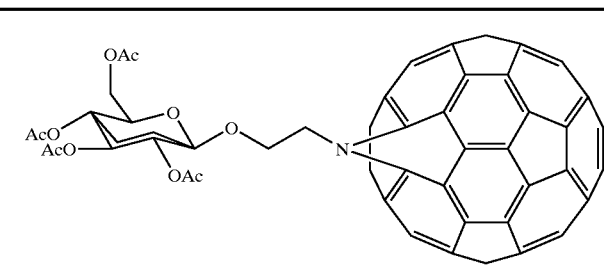 (D-AcGlc-(CH$_2$)$_2$—N)C$_{60}$ |

TABLE 1-continued
| Ex. No. | formula |
|---|---|
| | 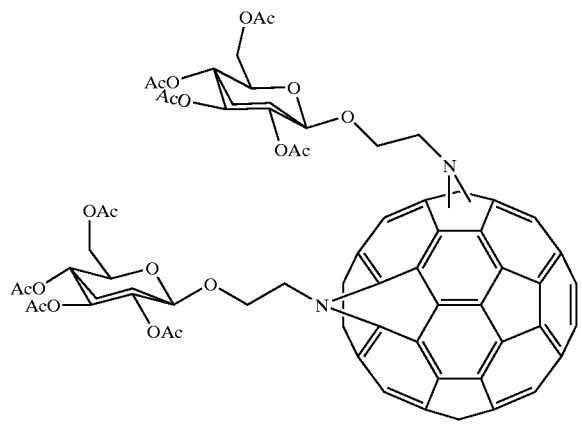
(D-AcGlc-(CH$_2$)$_2$—N)C$_{60}$ |
| 2 | 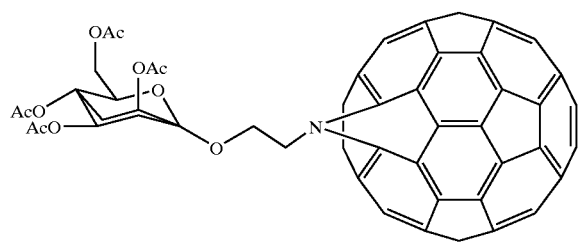
(D-AcMan-(CH$_2$)$_2$—N)C$_{60}$ |
| | 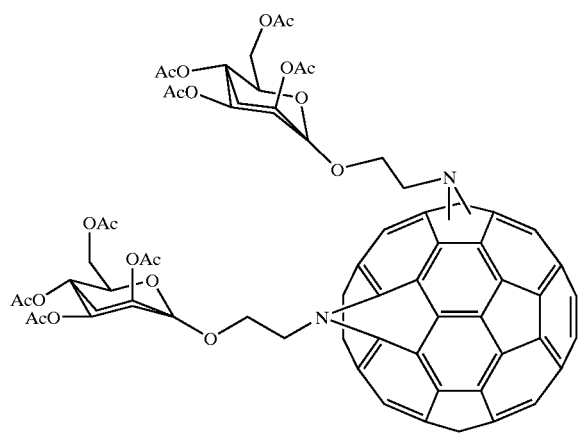
(D-AcMan-(CH$_2$)$_2$—N)$_2$C$_{60}$ |
| 3 | 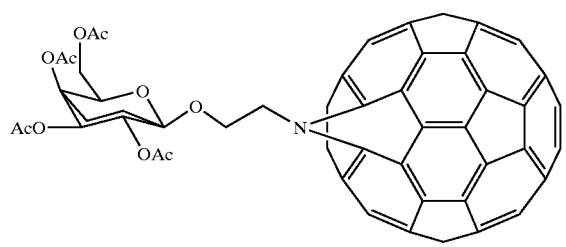
(D-AcGal-(CH$_2$)$_2$—N)C$_{60}$ |

TABLE 1-continued
| Ex. No. | formula |
|---|---|
| | 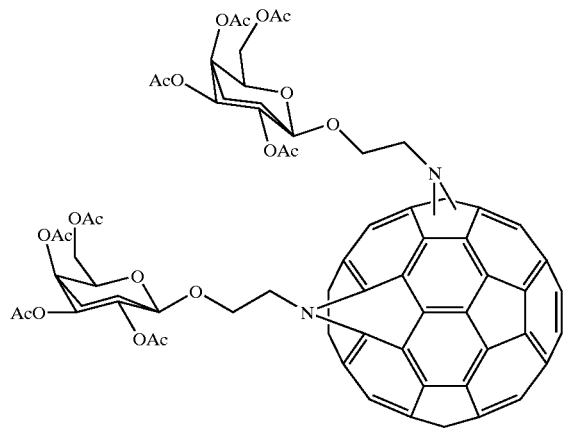
(D-AcGal-(CH$_2$)$_2$—N)$_2$C$_{60}$ |
| 4 | 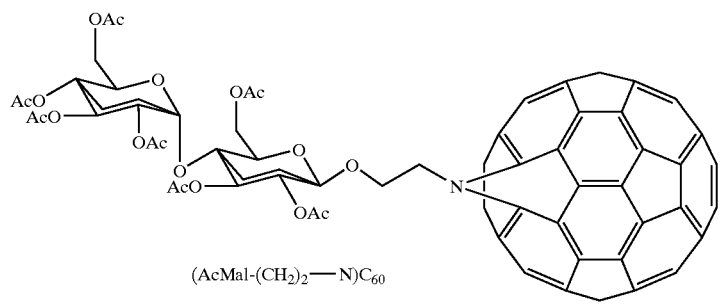
(AcMal-(CH$_2$)$_2$—N)C$_{60}$ |
| | 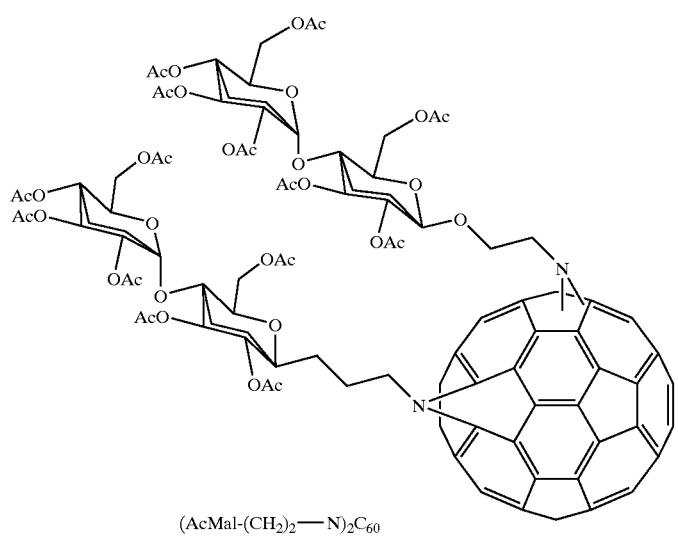
(AcMal-(CH$_2$)$_2$—N)$_2$C$_{60}$ |
| 5 | 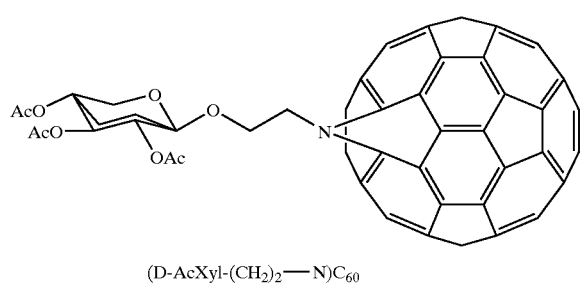
(D-AcXyl-(CH$_2$)$_2$—N)C$_{60}$ |

TABLE 1-continued
| Ex. No. | formula |
| --- | --- |
|  | 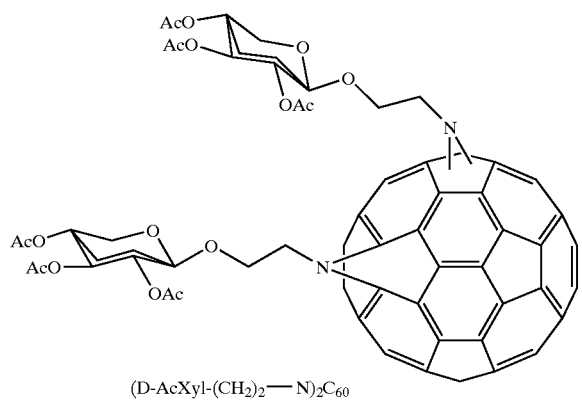 (D-AcXyl-(CH$_2$)$_2$—N)$_2$C$_{60}$ |
| 6 | 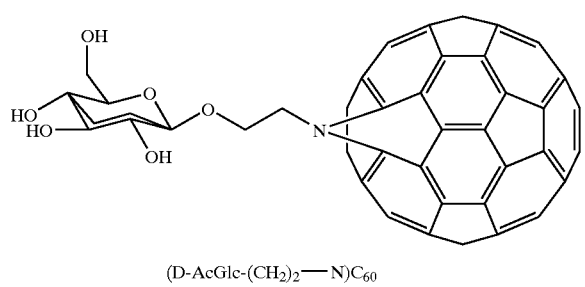 (D-AcGlc-(CH$_2$)$_2$—N)C$_{60}$ |
| 7 | 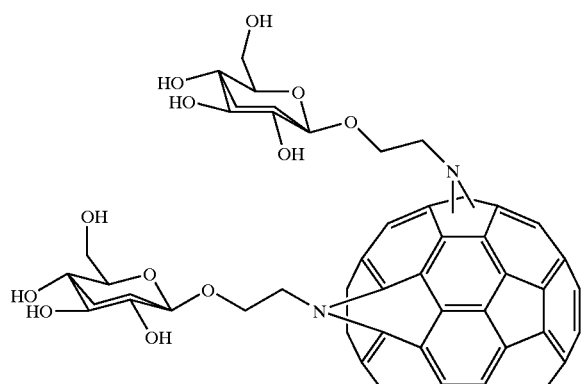 (D-AcGlc-(CH$_2$)$_2$—N)C$_{60}$ |
| 8 | 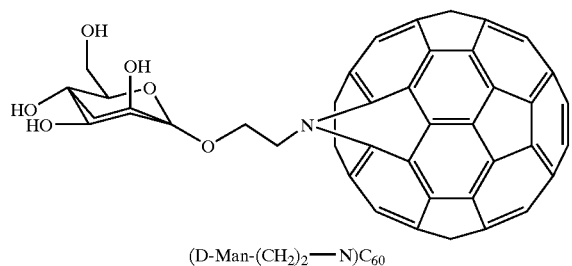 (D-Man-(CH$_2$)$_2$—N)C$_{60}$ |

TABLE 1-continued
| Ex. No. | formula |
|---|---|
| 9 | 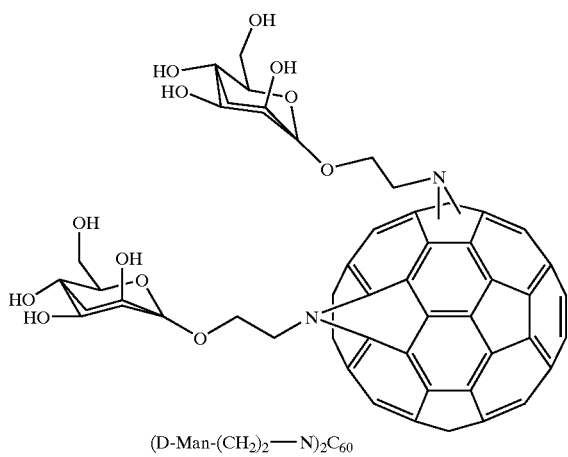 (D-Man-(CH$_2$)$_2$—N)$_2$C$_{60}$ |
| 10 | 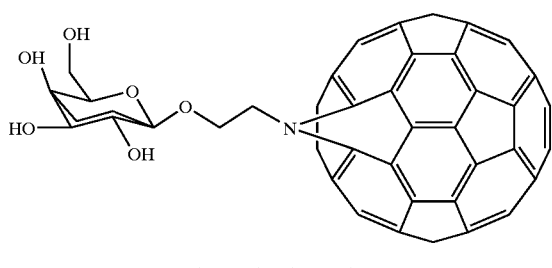 (D-Gal-(CH$_2$)$_2$—N)C$_{60}$ |
| 11 | 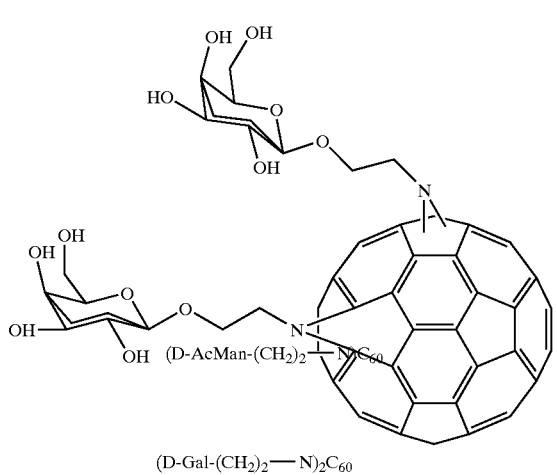 (D-Gal-(CH$_2$)$_2$—N)$_2$C$_{60}$ |
| 12 | 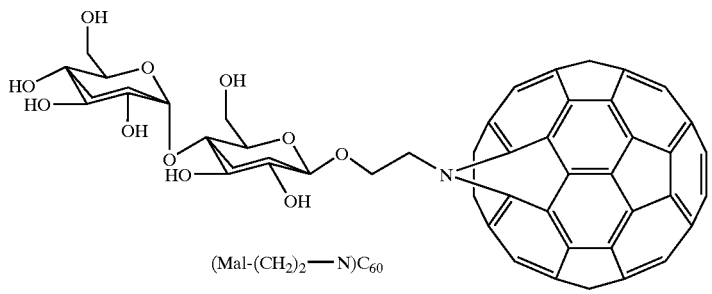 (Mal-(CH$_2$)$_2$—N)C$_{60}$ |

TABLE 1-continued

| Ex. No. | formula |
|---|---|
| 13 | 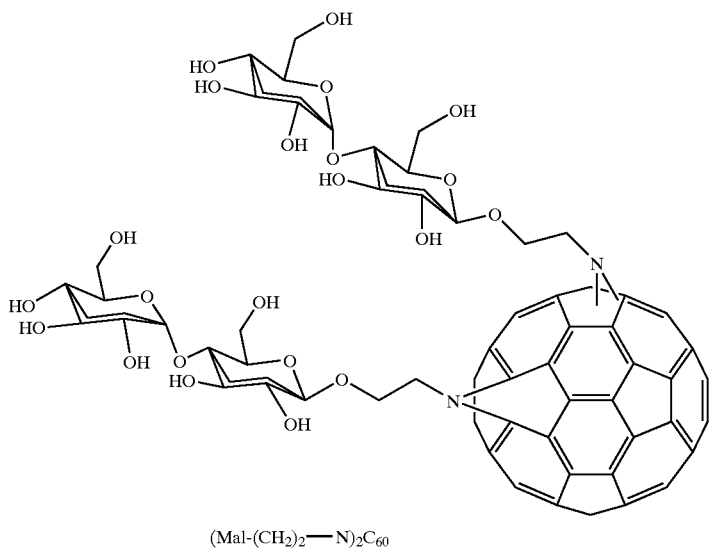
(Mal-(CH$_2$)$_2$—N)$_2$C$_{60}$ |
| 14 | 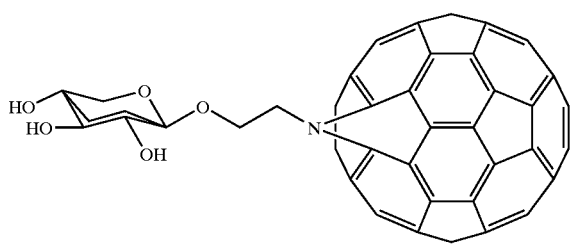
(D-Xyl-(CH$_2$)$_2$—N)C$_{60}$ |
| 15 | 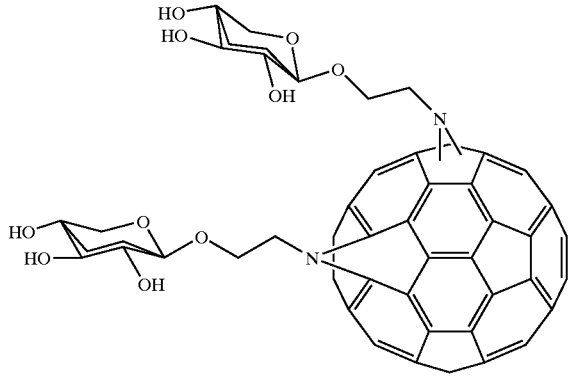
(D-Xyl-(CH$_2$)$_2$—N)$_2$C$_{60}$ |

Test Example 1
Quantum Yield Measurement of Singlet Oxygen

A DMSO solution containing $5.5 \times 10^{-5}$ M of 1,3-diphenylisobenzofuran (DPBF) was prepared, maintaining the water temperature in a waterbath at 27° C. 3 mL of the DMSO solution was poured into a quartz cell and a DMSO solution containing $1.5 \times 10^{-5}$ M of fullerene derivatives was added so that the concentration of the resulting solution is set to $6.5 \times 10^{-7}$ M. Subsequently, oxygen was bubbled through the solution for one minute or more. The cell was set in position within the waterbath, stirred using a multistirrer and irradiated with light every ten seconds to measure the absorbance of the DPBF at 418 nm. Natural logarithm of the absorbance thus measured was plotted against time of light irradiation to find the gradient. Thus, a relative scale with respect to the quantum yield of tetraphenylporphyrin ($\phi^1 O_2$) was calculated. The results are shown in Table 2.

TABLE 2

| Ex. | Compound | Relative scale for $\phi^1O_2$ | Ex. | Compound | Relative scale for $\phi^1O_2$ |
|---|---|---|---|---|---|
| 1 | (D-AcGlc-(CH$_2$)$_2$—N)C$_{60}$ | 0.6 | 6 | (D-Glc-(CH$_2$)$_2$—N)C$_{60}$ | 0.6 |
|  | (D-AcGlc-(CH$_2$)$_2$—N)$_2$C$_{60}$ | 0.5 | 7 | (D-Glc-(CH$_2$)$_2$—N)$_2$C$_{60}$ | 0.6 |
| 2 | (D-AcMan-(CH$_2$)$_2$—N)C$_{60}$ | 0.8 | 8 | (D-Man-(CH$_2$)$_2$—N)C$_{60}$ | 0.5 |
|  | (D-AcMan-(CH$_2$)$_2$—N)$_2$C$_{60}$ | 0.7 | 9 | (D-Man-(CH$_2$)$_2$—N)$_2$C$_{60}$ | 0.5 |
| 3 | (D-AcGal-(CH$_2$)$_2$—N)C$_{60}$ | 0.7 | 10 | (D-Gal-(CH$_2$)$_2$—N)C$_{60}$ | 0.7 |
|  | (D-AcGal-(CH$_2$)$_2$—N)$_2$C$_{60}$ | 0.5 | 11 | (D-Gal-(CH$_2$)$_2$—N)$_2$C$_{60}$ | 0.7 |
| 4 | (AcMal-(CH$_2$)$_2$—N)C$_{60}$ | 0.7 | 12 | (Mal-(CH$_2$)$_2$—N)C$_{60}$ | 0.7 |
|  | (AcMal-(CH$_2$)$_2$—N)$_2$C$_{60}$ | 0.6 | 13 | (Mal-(CH$_2$)$_2$—N)$_2$C$_{60}$ | 0.8 |
| 5 | (D-AcXyl-(CH$_2$)$_2$—N)C$_{60}$ | 0.4 | 14 | (D-Xyl-(CH$_2$)$_2$—N)C$_{60}$ | 0.3 |
|  | (D-AcXyl-(CH$_2$)$_2$—N)$_2$C$_{60}$ | 0.3 | 15 | (D-Xyl-(CH$_2$)$_2$—N)$_2$C$_{60}$ | 0.3 |
| Comp. | tetraphenylporphyrin | 1.0 | — | — | — |

The results in Table 2 indicate that the compounds of the present invention generated singlet oxygen effectively.

Test Example 2

Phototoxicity Test 1

The cytotoxicity of (Mal-(CH$_2$)$_2$—N)C$_{60}$ (hereafter, referred to as Compound A) obtained in Example 12 was evaluated by the viability of HeLa cells using an MTT assay (Carmichal, J., W. G. DeGraff, A. F.Gazdar, J. D. Minna and J. B. Mitchell, Cancer Res., 1987, 47, 936–942). HeLa cells (5×10$^3$ cells/well) were incubated in a Dulbecco's modified Eagle's medium (DMEM) containing 10% fetal bovine serum (FBS) on a 96-well plate in 5% CO$_2$ at 37° C. for 24 hours. After washing with phosphate buffered saline (PBS), 100 μl of (Mal-(CH$_2$)$_2$—N) C$_{60}$ (DMEM) (-) solution (25 μM) as a fullerene derivative of the present invention was added to the cells, which were incubated for two hours. The cells were washed with PBS, replaced with 100 μl of DMEM(+) and theie viability was measured using the MTT assay. The viability was determined by measuring the absorbance at 570 nm (OD570). FIG. 1 shows the survival ratio (%) of cells without light irradiation. The ratio was calculated by the following formula: Cell survival ratio (%)=(OD 570 in the presence of Compound A/OD 570 in the absence of Compound A)×100. A cell survival ratio of 100% means the absence of cytotoxicity. The ratio is considered to indicate the cytotoxicity of Compound A. FIG. 1 clearly shows that the cytotoxicity is not observed without light irradiation in the presence of Compound A.

HeLa cells (5×10$^3$ cells/well) were treated in the same manner as in the above. Compound A was added to the cells and the resulting cell was irradiated with a 500 W halogen lamp for 8 minutes. After 24 hours' incubation, the supernatant was removed and formazan was dissolved in 100 μl of DMSO. Thereafter, the viability was determined by measuring the absorbance at 570 nm (OD570). FIG. 1 shows the survival ratio (%) of the cells after the irradiation. The ratio was calculated by the following formula: Cell survival ratio (%)=(OD 570 in the presence of Compound A with irradiation/OD 570 in the absence of Compound A with irradiation)×100. FIG. 1 clearly shows that the cytotoxicity is observed when irradiated with light in the presence of Compound A.

Test Example 3

Phototoxicity Test 2

Figure 2:
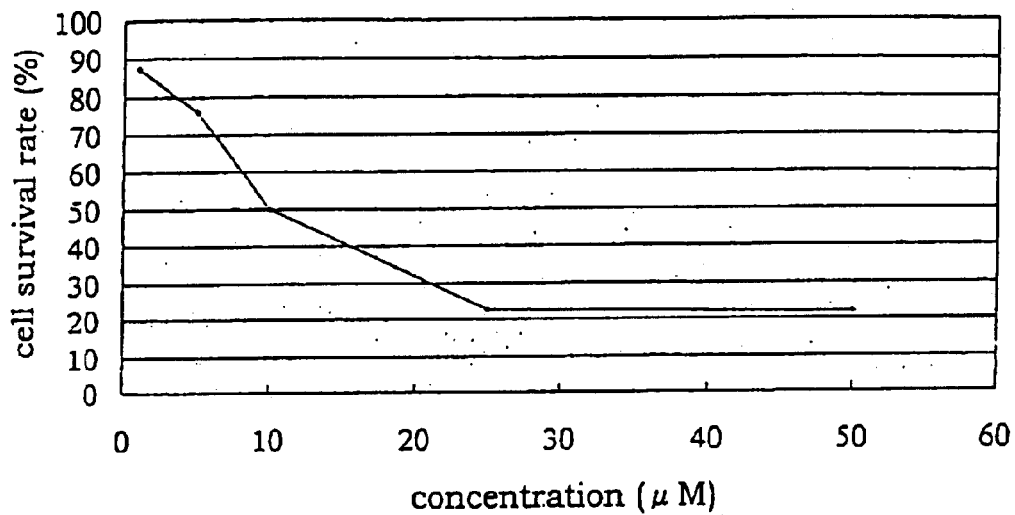
FIG. 2 is a graph showing photocytotoxicity of a fullerene derivative ($Mal\text{-}(CH_2)_2\text{-}N)C_{60}$ in the present invention.
Figure 3:
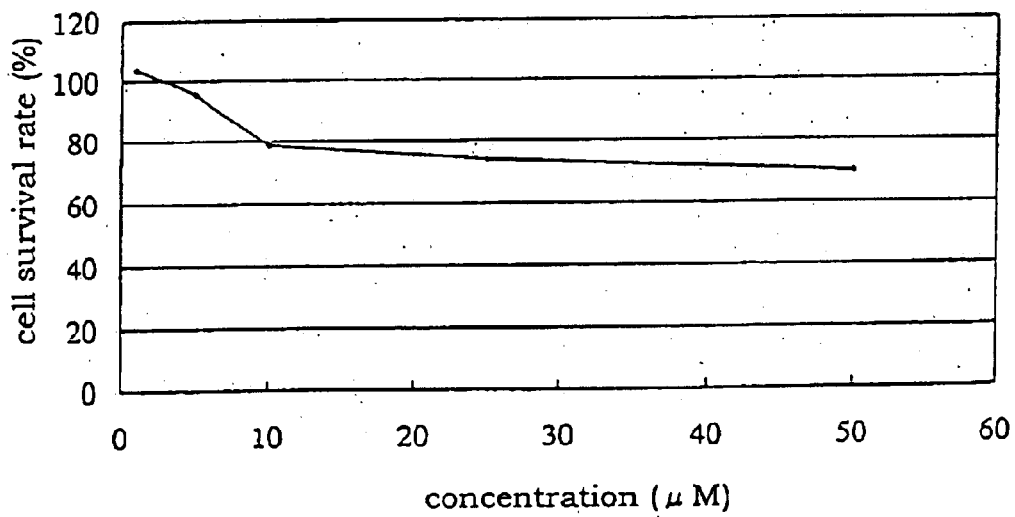
FIG. 3 is a graph showing photocytotoxicity of a fullerene derivative ($D\text{-}Xyl\text{-}(CH_2)_2\text{-}N)C_{60}$ in the present invention.

Evaluations were made in the same manner as in Test Example 2 except that each of (Mal-(CH$_2$)$_2$—N)C$_{60}$ (Compound A) obtained in Example 12 and (D-Xyl-(CH$_2$)$_2$—N)C$_{60}$ (hereafter, referred to as Compound B) obtained in Example 14 was used in amounts 1, 5, 10, 25 and 50 g M. The obtained results of the cytotoxicities of Compounds A and B are shown in FIGS. 2 and 3, respectively. As seen from FIG. 2, Compound A having a low concentration of 10 μM exhibited the toxicity in about 50% of the cells.

Industrial Applicability

The fullerene derivatives (I) and their salts of the present invention are more hydrophilic and lipophilic due to the introduction of the sugar residues and lower alkylene groups and are expected to have selectivity to tumor cells by cell recognition due to the sugar residues. Furthermore, because they are not toxic to the cells in a dark place, and have a cytocidal effect by light irradiation, the fullerene derivatives (I) and their salts of the present invention are useful as photosensitizers for PDT and PDD.

Further, the fullerene derivatives or their salts of the present invention are also usable as a heat-sensitizing paint.

What is claimed is:

1. A fullerene derivative represented by the formula (I):

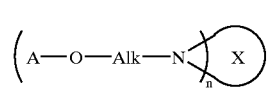

(I)

wherein, A is a residue of monosaccharides or disaccharides, and Alk is a lower alkylene group, the group represented by the formula (X):

(x)

is a fullerene residual skeleton, and n is an integral number of 1 or 2 or its salt.

2. A fullerene derivative according to claim 1, in which A is β-D-glucopyranosyl, α-D-mannopyranosyl, β-D-galactopyranosyl, β-D-xylopyranosyl or β-D-(glucopyranosyl-(1→4)-D-glucopyranosyl), Alk is an ethylene group, and the group represented by the formula (X) is a residual skeleton of fullerene-C$_{60}$, or its salt.

3. A composition for photosensitization comprising the fullerene derivative or its salt as set forth in claim 1 or 2.

4. A composition for photosensitization according to claim 3, which is used in photodynamic therapy.

* * * * *